(12) United States Patent
Strobel et al.

(10) Patent No.: US 8,080,256 B2
(45) Date of Patent: Dec. 20, 2011

(54) **ENDOPHYTIC FUNGI FROM *PTEROMISCHUM* SP. PLANT, COMPOUNDS AND METHODS OF USE**

(75) Inventors: Gary A. Strobel, Bozeman, MT (US); Yuhao Ren, Bozeman, MT (US); David B. Teplow, Tarzana, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 12/741,804

(22) PCT Filed: Nov. 6, 2008

(86) PCT No.: PCT/US2008/082678
§ 371 (c)(1),
(2), (4) Date: May 6, 2010

(87) PCT Pub. No.: WO2009/061950
PCT Pub. Date: May 14, 2009

(65) Prior Publication Data
US 2010/0266641 A1    Oct. 21, 2010

Related U.S. Application Data

(60) Provisional application No. 60/986,946, filed on Nov. 9, 2007.

(51) Int. Cl.
*A61K 39/00*    (2006.01)

(52) U.S. Cl. .................... 424/274.1; 530/300; 530/350; 530/820; 530/823; 514/3.3

(58) Field of Classification Search ........................ None
See application file for complete search history.

(56) References Cited

U.S. PATENT DOCUMENTS

| | | | |
|---|---|---|---|
| 6,613,738 B1 | 9/2003 | Strobel | |
| 7,232,565 B2 * | 6/2007 | Henson et al. | 424/93.5 |
| 2005/0260182 A1 | 11/2005 | Strobel | |

OTHER PUBLICATIONS

Wang, et al. (2006) "Neoplaether, a New Cytotoxic and Antifungal Endophyte Metabolite from Neoplaconema Napellum IFB-E016" FEMS Microbiol. Lett 261, 218-223.
Ren, et al. (2008) "Colutellin A, an Immunosuppressive Peptide from Colletotriachum Dematium" Microbiology 154, 1973-1979.
Feng W. Wang et al. 'Neoplaether, a new cytotoxic and antifungal endophyte metabolite from *Neoplaconema napellum* IFB-E016.' FEMS Microbiol Lett. vol. 261, No. 2, pp. 218-223 (Aug. 2006).
Yuhao Ren et al. 'Colutellin A, an immunosuppressive peptide from *Colletotriebum dematium*,' Microbiology, vol. 154, pp. 1973-1979 (Jul. 24, 2008).
International Search Report for PCT/US2008/082678, mailed Jun. 30, 2009.

* cited by examiner

*Primary Examiner* — Jennifer Graser
(74) *Attorney, Agent, or Firm* — Suzannah K. Sundby, Esq.; Smith, Gambrell & Russell, LLP

(57) ABSTRACT

The present disclosure relates to endophytic fungi from higher plants such as a *Pteromischum* sp. plant, and to extracts and compounds from such fungi that have desirable biological activities, such as antifungal and immunosuppressive activities. The present disclosure further relates to compositions comprising such extracts and compounds, as well as methods of making and using the compositions.

9 Claims, 4 Drawing Sheets

SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 1
tccgtaggtg aacctgcgg                                            19

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 2
tcctccgctt attgatatgc                                           20

<210> SEQ ID NO 3
<211> LENGTH: 4
<212> TYPE: PRT
<213> ORGANISM: colletotrichum dematium

<400> SEQUENCE: 3

Val Ile Ser Ile
1

ENDOPHYTIC FUNGI FROM *PTEROMISCHUM* SP. PLANT, COMPOUNDS AND METHODS OF USE

CROSS REFERENCE TO RELATED APPLICATION

This application is a 371 U.S. National Phase Application of PCT/US2008/082678, filed Nov. 6, 2008, and claims the benefit of U.S. Provisional Patent Application No. 60/986,946 filed on Nov. 9, 2007, which is herein incorporated by reference in its entirety.

FIELD OF THE DISCLOSURE

The present disclosure relates to endophytic fungi from higher plants such as a *Pteromischum* sp. plant, and to extracts and compounds from such fungi that have desirable biological activities, such as antifungal and immunosuppressive activities. The present disclosure further relates to compositions comprising such extracts and compounds, as well as methods of making and using the compositions.

BACKGROUND OF THE DISCLOSURE

Endophytes, microorganisms that reside in the tissues of living plants, are relatively unstudied and potential sources of novel natural products for exploitation in medicine, agriculture and industry. It is worthy to note, that of the nearly 300,000 plant species that exist on the earth, each individual plant is host to one or more endophytes. Only a handful of these plants have ever been completely studied relative to their endophytic biology. Consequently, the opportunity is great to find new and interesting endophytic microorganisms among myriads of plants in different settings, and ecosystems.

Currently, endophytes are viewed as an outstanding source of bioactive natural products because there are so many of them occupying literally millions of unique biological niches (higher plants) growing in so many unusual environments. While the symptomless nature of the occupation of plant tissues by endophytes has prompted focus on symbiotic or mutualistic relationships between endophytes and their hosts, the observed biodiversity of endophytes suggests they can also be aggressive saprophytes or opportunistic pathogens. Both fungi and bacteria are the most common microbes existing as endophytes (Bacon and White, *Microbial Endophytes*. Marcel Dekker Inc., N.Y., 2000). For example, some of these organisms make compounds now exploitable as anticancer drugs, antibiotics, and antioxidants.

There is a need for more and better antimycotics, as the human population is developing more fungal infections. This is particularly an issue with immunosuppressed patients, such as HIV/AIDS patients, patients with organ-transplants, and anyone who must take immunosuppressive drugs. In both cases, patients with these difficulties have immune systems that are weakened. Antifungal agents that are currently available, such as cyclosporin A, are toxic to the subject, and often ineffective against the fungal pathogen.

Since the discovery of cyclosporin A from *Trichoderma polysporum* in 1976, it has been the principal immunosuppressive agent used in medicine (Ruegger et al., *Hel. Chim. Acta.* 59: 1075-1092, 1976). Presently, cyclosporin A, along with tacrolimus (FK506) and sirolimus (rapamycin) are three immunosuppressants which act on $CD4^+$ T cells used in clinical practice. These compounds have gained wide spread acceptance for use in organ and tissue transplantation, various autoimmune diseases and with some other non-autoimmune inflammatory diseases. However, all three drugs can cause nephrotoxicity (Daoud et al., *Epilepsia* 48: 834-836, 2007). In addition, cyclosporin A and tacrolimus can cause neurotoxicity and beta-cell toxicity (Tanabe, *Drugs* 63: 1535-48, 2003; Froud et al., *Cell Transplant* 15: 613-620, 2006). Cyclosporin A can cause more serious nephrotoxicity, hypertension and hyperlipidaemia in comparison to tacrolimus (Andoh et al., *Kidney Int.* 50: 1110-1117, 1996). Novel compounds with low toxicity that act in an effective and useful manner will contribute to the arsenal of substances that act to suppress the immune system and will be especially helpful to those with autoimmune diseases and organ recipients.

There is also a need for environmentally sound ways to control pests and pathogens (Overton, *Ecologically Based Pest Management—New Solutions for a New Century*. Natl. Aca. Press. Washington D.C., 1996). In the past, the major source of pesticidal agents came from organic synthesis. Recently, interest has increased for using more environmentally friendly methods in agricultural production, including naturally-occurring biological compounds.

SUMMARY

Provided herein is an endophytic *Colletotrichum* (previously known as *Volutella*) sp., associated with a *Pteromischum* sp. plant growing in a tropical forest in Costa Rica, which is capable of producing antifungal or immunosuppressant compounds. In an example, a specific *Colletotrichum* sp. isolate, referred to as isolate C-12, is disclosed that possesses antifungal and immunosuppressant activities. For example, the disclosed isolate C-12 was capable of inhibiting pathogenic fungi including *Botrytis cinerea, Sclerotinia sclerotiorum*, or *Rhizoctonia solani*.

The present disclosure also relates to extracts, compositions and compounds generated from endophytic *Colletotrichum* sp. isolates, such as isolate C-12, including specifically, extracts, compositions and compounds that have immunosuppressive or antimycotic activity. For example, exemplary compounds can include cyclic lipopetides with antimycotic and immunosuppressive activities.

The present disclosure further relates to methods for producing a biological agent, including an endophytic *Colletotrichum* sp.; an extract of an endophytic *Colletotrichum* sp.; or a compound obtained from the endophyte (e.g., a compound or mixture of compounds having antimycotic, immunosuppressive, or other biological activity). In an example, the method includes cultivating a strain of endophytic *Colletotrichum* sp. and recovering the biological agent from the culture medium or from an extract prepared from *Colletotrichum* cells.

Also provided are methods of suppressing an immune response in a subject, such as a subject with an autoimmune disease, non-autoimmune inflammatory disease or in need of an organ or tissue transplant.

Additionally, methods of protecting plants against attack by a plant pathogen, such as fungi are provided. In an example, isolate C-12, including specifically extracts, compositions and compounds are used to treat fungal infections in plants.

The foregoing and other features will become more apparent from the following detailed description, which proceeds with reference to the accompanying figures.

BRIEF DESCRIPTION OF THE DRAWINGS

FIG. 1 is a digital image of an exemplary environmental scanning electron microscope (SEM) image of the sporodochial fruiting structure of *Colletotrichum* sp. isolate C-12 along with conidiospores and setae protruding from the structure (bar 20 μM). The inset shows a point dried image (bar 50 μM).

FIG. 2 is a digital image of a proton nuclear magnetic resonance (NMR) spectrum of colutellin A taken in 100% deuterated methanol. The spectrum is consistent with that of a lipopeptide, with many methyl and methylene resonances at 0.7-2.0 p.p.m. and other proton resonances on carbons bearing nitrogen and oxygen further downfield.

FIG. 3 is a digital image of a mass spectrum of compounds taken by Fourier transform ion cyclotron resonance (FTICR). Two clusters of ions were detected, one protonated and the other sodiated. M1=1081.7, M2=1095.7, M3=1111.7, M4=1127.7 (M4 isotopic peak is well resolved in LC/MS). Since this spectrum represents the masses of the entire broad silica gel column/HPLC peak, the $M4^+$ $Na^+$ peak is minimized.

FIG. 4 includes graphs illustrating that colutellin A (denoted by a square) is less toxic to human peripheral blood mononuclear cells (PBMCs) than is cyclosporin A (denoted by an enclosed diamond). Human PBMCs were treated with varying concentrations of colutellin A, cyclosporin A or equivalent amounts of DMSO (carrier), denoted by triangle for 24 and 48 hours. The cells (PBMCs) were then stained with 7-AAD and Annexin V directly conjugated to FITC or PE and subjected to flow cytometry. The percentage of necrotic (7-AAD+/Annexin V+), apoptotic (7-AAD−/Annexin V+) and viable (7-AAD−/Annexin V−) cells were calculated using CellQuest software (BD Biosciences). Data is representative of multiple studies. Error bars represent standard deviations between triplicate treatment groups.

SEQUENCE LISTING

The nucleic acid and protein sequences listed in the accompanying sequence listing are shown using standard letter abbreviations for nucleotide bases, as defined in 37 C.F.R. 1.822. Only one strand of each nucleic acid sequence is shown, but the complementary strand is understood as included by any reference to the displayed strand.

SEQ ID NO: 1 is an amino acid sequence included with collutelin A.

SEQ ID NOS: 2 and 3 are oligonucleotide primer sequences used to detect the ITS regions of *C. dematium* fungus.

DETAILED DESCRIPTION OF SEVERAL EMBODIMENTS

I. Terms and Abbreviations

Abbreviations

- AMU: Atomic Mass Unit
- ESEM: Environmental Scanning Electron Microscope
- FTICR: Fourier transform ion cyclotron resonance
- HPLC: High Pressure Liquid Chromatography
- LC/MS: Liquid Chromatography/Mass Spectrometry
- MIC: Minimum Inhibitory Concentrations
- NMR: Nuclear Magnetic Resonance
- PBMC: Peripheral Blood Mononuclear Cell
- SEM: Scanning Electron Microscope
- UV: Ultraviolet Terms Unless otherwise noted, technical terms are used according to conventional usage. Definitions of common terms in molecular biology may be found in Benjamin Lewin, Genes VII, published by Oxford University Press, 2000 (ISBN 019879276X); Kendrew et al. (eds.), The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all amino acid sizes and molecular weight or molecular mass values given for the polypeptides are approximate and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Administer: To provide or give a subject an agent, such as colutellin A, by any effective route. Administration can be systemic or local. Exemplary routes of administration include, but are not limited to, oral, injection (such as subcutaneous, intramuscular, intradermal, intraperitoneal and intravenous), sublingual, rectal, transdermal (e.g., topical), intranasal, vaginal and inhalation routes. For example, if the chosen route is intravenous, the composition is administered by introducing the composition into a vein of the subject, and if the chosen route is intramuscular, the compositing is administered by introducing the composition in to a muscle. In particular examples, agents (such as those including colutellin A) are administered to a subject having or at risk of developing a fungal infection, an autoimmune disease, a non-autoimmune inflammatory disorder or rejecting an organ or tissue transplant.

Agent: Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional agent induces the desired response (such as inducing a therapeutic or prophylactic effect when administered to a subject). In an example, an agent includes an endophytic *Colletotrichum* sp. isolate, such as isolate C-12. In a particular example, an agent includes colutellin A.

Antimycotic: An agent that suppresses, inhibits, prevents or destroys the growth of fungi.

Autoimmune disease: A disease in which the immune system produces an immune response (for example, a B cell or a T cell response) against an antigen that is part of the normal host (that is, an autoantigen), with consequent injury to tissues. An autoantigen may be derived from a host cell, or may be derived from a commensal organism such as the micro-organisms (known as commensal organisms) that normally colonize mucosal surfaces.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like.

Figure 1:
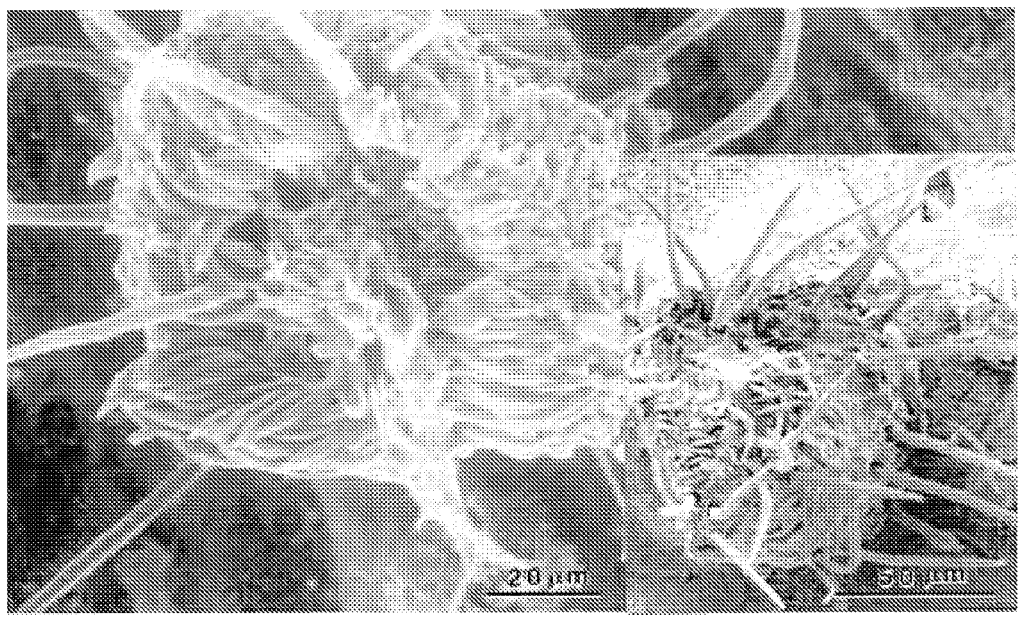

Biological Activity: An expression describing the effect of a substance such as an extract, composition or compound on living matter. In an example, biological activity includes at least one of antifungal or immunosuppressive activity. In one example, the extract, composition or compound includes at least one specific endophytic *Colletotrichum* sp. isolate which has antifungal or immunosuppressive activity. For example, the extract, composition or compound includes at least colutellin A (molecular mass of 1127.7) which has antifungal and immunosuppressive activity.

*Botrytis cinerea*: A fungus that affects many plant species, including wine grapes. In viticulture, it is commonly known as botrytis bunch rot; in horticulture, it is usually called grey mould or gray mold. The fungus gives rise to two different kinds of infections on grapes. The first, grey rot, is the result of consistently wet or humid conditions, and typically results in the loss of the affected bunches. The second, noble rot, occurs when drier conditions follow wetter, and can result in distinctive sweet dessert wines, such as Sauternes or the Aszú of Tokaj.

*Colletotrichum dematium*: An endophytic fungus that has inhibitory activity to *Botrytis cinerea*. *Colletrotrichum* has the same fruiting structure as *Volutella*. In the past, *Colletotrichum* sps., such as *C. dematium*, have been distinguished from *Volutella* by their pathogenic activity whereas *Volutella* are non-pathogenic. Recently, non-pathogenic examples of *Colletotrichum* sps. have been identified.

Described herein is a *C. dematium* fungus designated CR-12 (rDNA sequence for CR-12 GenBank accession number EU3330193) that produces the novel peptide antimycotic, colutellin A. Colutellin A is a cyclic lipopeptide with a molecular mass of 1127.7, possesses bioactivities at least against fungi (such as *Botrytis cinerea* and *Sclerotinia sclerotiorum*) as well as immunosuppressive activities (including inhibiting the production of IL-2 from CD4). Colutellin A is the same compound that was disclosed in U.S. Patent Application No. 60/986,946 filed on Nov. 9, 2007, but referred to therein as volutellin A. Based on initial taxonomic studies, the compound was termed volutellin A because it was believed to be produced from a *Volutella* sp. fungus. However, further molecular studies indicated that the fungus was *C. dematium* and not a *Volutella* sp. Therefore, the compound was renamed to reflect this distinction.

Cultivation: Intentional growth of an organism, such as an endophytic *Colletotrichum* sp., in the presence of assimilable sources of carbon, nitrogen and mineral salts. In an example, such aerobic growth can take place in a solid or semi-solid nutritive medium, or in a liquid medium in which the nutrients are dissolved or suspended. In a further example, the cultivation may take place on a surface or by submerged culture. The nutritive medium can be composed of complex nutrients or can be chemically defined.

Disease: An abnormal condition of an organism that impairs bodily functions.

Endophyte: Plant-associated microorganisms that live in the interstitial spaces of living plant tissues (Bacon & White, *Microbial Endophytes*. Marcel Deker Inc., N.Y., 2000). Higher plants may host one or more endophytic microbes, which include fungi, bacteria, and actinomycetes. Endophytes reside in the tissues beneath the epidermal cell layers. It is well understood that endophytic infections or associations are inconspicuous (Id.). As a result, the host tissues are transiently symptomless and colonization of the tissues is internal to the surface of the plant. The exact physical relationship of the endophyte to the plant remains obscure, because it is extremely difficult, for example, by electron microscopic techniques, to find an endophyte within plant tissues. The relationship that any given endophyte establishes with the plant likely varies from truly symbiotic to something bordering on pathogenic. In an example, a specific endophyte such as an endophytic *Colletotrichum* sp. is isolated from one or more plants in which the endophytic *Colletotrichum* sp. produces antimycotic, immunosuppressive activities or other biologically active compounds of interest.

Immune response: A response of a cell of the immune system, such as a B-cell, T-cell, macrophage or polymorphonucleocyte, to a stimulus such as an antigen. An immune response can include any cell of the body involved in a host defense response for example, an epithelial cell that secretes an interferon or a cytokine. An immune response includes, but is not limited to, an innate immune response or inflammation.

Immunosuppression: An act or event that reduces the activation or efficacy of the immune system. For example, immunosuppression is generally done to prevent the body from rejecting an organ transplant, treating graft-versus-host disease after a bone marrow transplant, or for the treatment of autoimmune diseases such as rheumatoid arthritis or Crohn's disease. In an example, an agent including colutellin A is administered to a subject in need of immunosuppression.

Inhibit: To decrease, limit or block the action or function of a molecule. In an example, the production of IL-2 is decreased, limited or block by colutellin A. For example, the colutellin A inhibits, reduces or decreases IL-2 production, such as by a decrease of at least 10%, at least 20%, at least 50%, at least 70%, or even at least 90%.

Mutant strain: A strain which arises spontaneously or through the effect of an external agent whether that agent is applied deliberately or otherwise.

Parental strain: The original endophytic *Colletotrichum* sp. strain, for instance before mutagenesis (which leads to the mutated strain) or genetic engineering (which leads to an engineered strain).

*Rhizoctonia solani*: A basidiomycete fungus which primarily attacks below ground plant parts such as the seeds, hypocotyls, and roots, but is also capable of infecting above ground plant parts (e.g., pods, fruits, leaves and stems). The most common symptom of Rhizoctonia disease is referred to as "damping-off" characterized by non germination of severely infected seed whereas infected seedlings can be killed either before or after they emerge from the soil. Infected seedlings not killed by the fungus often have cankers, which are reddish-brown lesions on stems and roots.

*Sclerotinia sclerotiorum*: A fungus that is capable of infecting numerous crops including lettuce, broccoli, cabbage, cauliflower, carrots, celery, beans, tomato, peppers, potatoes, stocks, sunflower, eggplant, squash, artichoke, asparagus, beet, broad bean, flower crops and landscape shrubs. A typical initial symptom of *S. sclerotiorum* is the presence of a cottony, white, dense mat of mycelial growth (mass of fungus strands) on the surface of the host and on the adjacent soil surface. Within this fluffy white mass, dense white bodies of fungus soon form. These bodies become black and hard as they mature and are called sclerotia. The sclerotia act like seeds and allow the fungus to survive for several years in the soil.

Subject: Living multi-cellular vertebrate organisms, a category that includes human and non-human mammals (such as laboratory or veterinary subjects). In an example, a subject is a human. In an additional example, a subject is selected that is in need of immunosuppression.

Suppress (or decrease): To reduce the quality, amount, or strength of something. In one example, a therapy suppresses or reduces an immune response or one or more symptoms associated with an immune response, for example as compared to the response in the absence of the therapy. In a particular example, a therapy suppresses an immune response by at least 10%, at least 20%, at least 50%, at least 70%, or even at least 90%. Such suppression can be measured using methods disclosed herein.

Substantially pure or Purified: A peptide, protein, or other active compound that has been isolated from a cell, cell culture medium, or other crude preparation and subjected to fractionation to remove various components of the initial preparation, such as proteins, cellular debris, and other components. Such purified preparations can include materials in covalent association with the active agent, such as glycoside residues or materials admixed or conjugated with the active biologically active agent, which may be desired to yield a modified derivative or analog of the active agent or produce a combinatorial therapeutic formulation, conjugate, or the like. The term purified thus includes such desired products as biologically active compounds wherein additional compounds or moieties are bound to the biologically active agent in order to allow for the attachment of other compounds and/or provide for formulations useful in therapeutic treatment or diagnostic procedures.

Generally, substantially purified peptides, proteins, or other active compounds include more than 50%, for instance more than 80%, of all macromolecular species present in a preparation prior to admixture or formulation of the respective compound with additional ingredients in a complete pharmaceutical formulation for therapeutic administration. Additional ingredients can include a pharmaceutical carrier, excipient, buffer, absorption enhancing agent, stabilizer, preservative, adjuvant or other like co-ingredients. More typically, the peptide, protein, or other active compound is purified to represent greater than 90%, often greater than 95% of all macromolecular species present in a purified preparation prior to admixture with other formulation ingredients. In other cases, the purified preparation may be essentially homogeneous, wherein other macromolecular species (contaminants) are less than 1%. In an example, a substantially pure *Colletotrichum* sp. compound is defined herein as a *Colletotrichum* sp. preparation (e.g., colutellin A (molecular mass of 1081.7), colutellin B (molecular mass of 1095.7), colutellin C (molecular mass of 1111.7) or colutellin D (molecular mass of 1127.7)) which contains at least 80% of at least one of these identified compounds or a combination thereof, such as at least 85%, 90% or 95% of at least one of the *Colletotrichum* sp. compounds, including, but not limited to compounds with a molecular mass of 1081.7, 1095.7, 1111.7, 1127.7 or a combination thereof.

T-Cell: A white blood cell critical to the immune response. T-cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T-cells carry the "cluster of differentiation 8" (CD8) marker. In one embodiment, a CD8 T-cell is a cytotoxic T lymphocyte. In another embodiment, a CD8 cell is a suppressor T-cell.

Therapeutically effective amount: An amount of an agent (such as an agent that includes colutellin A), that alone, or together with one or more additional therapeutic agents, induces the desired response, such as suppression of an immune response. In one example, it is an amount of an agent including colutellin A needed to prevent or delay an immune response, cause regression of an existing immune response or treat one or more signs or symptoms associated with an immune response, in a subject. Ideally, a therapeutically effective amount provides a therapeutic effect without causing a substantial cytotoxic effect in the subject. The preparations disclosed herein are administered in therapeutically effective amounts.

In an example, a desired response is to reduce or decrease an immune response associated with an organ and tissue transplantation, various autoimmune diseases, or certain non-autoimmune inflammatory diseases. For example, the agent can suppress the immune response by a desired amount, for example by at least 5%, at least 10%, at least 15%, at least 20%, at least 25%, at least 30%, at least 50%, at least 75%, or even at least 90%, as compared to a response in the absence of the agent.

The effective amount of an agent that includes colutellin A, that is administered to a human or veterinary subject will vary depending upon a number of factors associated with that subject, for example the overall health of the subject. An effective amount of an agent can be determined by varying the dosage of the product and measuring the resulting therapeutic response, such as the suppression of the immune response. Effective amounts also can be determined through various in vitro, in vivo or in situ immunoassays. The disclosed agents can be administered in a single dose, or in several doses, as needed to obtain the desired response. However, the effective amount of can be dependent on the source applied, the subject being treated, the severity and type of the condition being treated, and the manner of administration.

In particular examples, a therapeutically effective dose of an agent including colutellin A, colutellin B, colutellin C, colutellin D or a combination thereof includes at least 1 μg daily (such as 1-100 μg or 5-50 μg) if administered via injection, or at least 1 mg daily if administered topically (such as 1-100 mg or 5-50 mg) of the agent that includes the desired colutellin. In particular examples, such daily dosages are administered in one or more divided doses (such as 2, 3, or 4 doses) or in a single formulation.

The disclosed agents that include colutellin A can be administered alone, in the presence of a pharmaceutically acceptable carrier, in the presence of other therapeutic agents or both.

Under conditions sufficient for: A phrase that is used to describe any environment that permits the desired activity. In one example, includes treating cells (such as cells infected with a target pathogen) with a compound including at least one of the disclosed *Colletotrichum* sp. isolates sufficient to allow the desired activity. In particular examples, the desired activity is the inhibition of growth by the respective fungus. For example, the targeted pathogen is a fungus and the desired activity is to inhibit or at least reduce the growth of the fungus. In another example, the target is a cell involved in mounting or maintaining an immune response and the desired activity is to suppress or inhibit the immune response.

Unit Dosage Form: Physically discrete units suitable as unitary dosages for application to a subject (e.g., a human subject or animal, or a plant), each unit containing a predetermined quantity of active material calculated to produce the desired pharmaceutical effect in association with the required pharmaceutical diluent, carrier, or vehicle.

II. Overview of Several Embodiments

The current disclosure describes the isolation and identification of a *C. dematium* strain from *Pteromischum* sp. growing in a tropical forest in Costa Rica. This fungus is an endophyte that was identified on the basis of its morphological and genetic characteristics. Extracts of the fermentation broth of *C. dematium* possess selective antifungal activity associated with a novel antimycotic peptide that the inventors termed colutellin A. Characterization studies revealed that colutellin A inhibited production of interleukin 2 (IL-2) from activated $CD4^+$ T-cells, suggesting that it may have potential as a novel immunosuppressive drug. Surprisingly, in contrast to cyclosporin A, it possessed little or no cytotoxicity to human blood cells. These findings were reported in *Microbiology* 154: 1973-1979, 2008 which is hereby incorporated by reference in its entirety.

Based on these discoveries, disclosed herein is an endophytic fungus isolated from a *Pteromischum* sp. plant, wherein the isolated endophytic fungus has antifungal or immunosuppressive activity. In an example, the isolated endophytic fungus is a *Colletotrichum* sp. In one example, the fungus has biological activity against a fungal plant pathogen, such as *Botrytis cinerea, Sclerotinia sclerotiorum*, or *Rhizoctonia solani*. For instance, specifically the CR-12 strain of *C. dematium* is provided herein.

Also disclosed herein are crude extracts obtained from the endophytic fungus isolated from a *Pteromischum* sp. plant. In an example, the crude extract is isolated from an endophytic fungus (e.g., *C. dematium*, such as the CR-12 strain) that has biological activity against a fungal plant pathogen, such as *Botrytis cinerea, Sclerotinia sclerotiorum*, or *Rhizoctonia solani*.

Compounds produced by the disclosed isolated endophytic fungus are also provided. In an example, a compound has a molecular mass of 1081.7, 1095.7, 111.7 or 1127.7. In some examples, a compound includes the N-terminal tetrapeptide sequence Val-Ile-Ser-Ile (SEQ ID NO: 1).

Also disclosed are methods of suppressing an immune response. In an example, a method includes administering to a subject in need of immunosuppression a therapeutically effective amount of an agent including a disclosed endophytic fungus, crude extract isolated from a disclosed endophytic fungus or compound produced therefrom, thereby suppressing the immune response. In some examples, the method further includes first selecting a subject in need of immunosuppression.

Methods to protect a plant against a fungal pathogen, such as *Botrytis cinerea, Rhizoctonia solani*, and/or *Sclerotinia sclerotiorum* are provided. In an example, a method to protect a plant against a fungal pathogen includes treating the plant with an effective amount of a disclosed endophytic fungus, a crude extract isolated from a disclosed endophytic fungus or compound produced therefrom, thereby protecting the plant against the fungal pathogen. In some examples, the plant is treated by applying the strain directly to the plant. In other examples, the plant is treated by applying the strain to soil adjacent to the plant. In certain examples, the plant is treated by applying the strain to seed.

III. Isolated Endophytic Microorganisms

In the present disclosure, the isolation of specific endophytic *Colletotrichum* sp. that produce antimycotic, immunosuppressive or other biologically active compounds of interest involves selecting one or more plants as a source of the endophyte. In an example, the selection process is conducted on the basis of the environment, age, or natural history of a given plant. Such selection methods involve culturing tissue from the interior region of a dicotyledonous plant, e.g., *Pteromischum* sp. plant, on nutrient media for a time sufficient to permit colony formation by a strain of endophytic *Colletotrichum* sp. associated with the plant tissue and selecting one or more endophytic *Colletotrichum* sp. strains demonstrating the biological activity of interest. Various means can be used to select the endophytic *Colletotrichum* sp. isolates, and the isolates can be tested through any of numerous methods known in the art to discover a biological activity of interest, either by measuring some activity of the isolates directly, e.g., by zones of inhibition, or by preparing and testing extracts or purified compounds from the isolates.

In an example, the biological activity of interest can inhibit or suppress an immune response. In another example, the biological activity of interest can be to control or inhibit plant pathogens. For example, the biological activity is against fungi (such as *Botrytis cinerea, Sclerotinia sclerotiorum*, and *Rhizoctonia solani*).

In an example, endophytic *Colletotrichum* sp. isolates are isolated from a *Pteromischum* sp. For example, endophytic *Colletotrichum* sp. isolates can be isolated by fermentation and the broth extracted with an organic solvent, e.g., n-butanol, and the contents of the residue purified by bioassay guided high performance liquid chromatography using the fungus *Botrytis cinerea* as the test organism. In an example, a compound with a molecular mass of 1081.7, 1095.7, 1111.7, or 1127.7 is obtained.

IV. Biologically Active Agents

The present disclosure relates in certain embodiments to biologically active agents useful in treating or preventing various conditions. The biologically active agents in various examples are the *Colletotrichum* sp. isolates themselves, crude extracts obtained by cultivating such isolates under culture conditions, or compounds (such as peptides) isolated from the isolates. In an example, the biologically active agent includes at least one compound with a molecular mass of 1081.7, 1095.7, 1111.7, and 1127.7 or a combination of such compounds. For example, a biologically active agent includes colutellin A peptide (a cyclic lipopeptide with a molecular mass of 1127.7) and possesses bioactivities at least against fungi (such as *Botrytis cinerea* and *Sclerotinia sclerotiorum*) as well as immunosuppressive activities (including inhibiting the production of IL-2 from CD4). In this manner, the disclosure also provides novel biologically active extracts, compounds (e.g., a family of cyclic lipopeptides) and agents.

V. Uses of Biologically Active Compounds and Agents

The biologically active compounds of the present disclosure can be used to suppress an immune response or to control a pathogenic organism, such as a fungus. The agent, including one of the disclosed compounds, is provided in an amount effective to inhibit the pathogenic organism or condition for a time and under conditions permitting the agent to inhibit the pathogenic organism or condition.

The *Colletotrichum* sp. isolates have significant immunosuppressive and antifungal activity. In an example, the biologically active agents can be used to suppress an immune response. For example, a biologically active agent including an endophytic *Colletotrichum* sp. compound with a molecular mass of 1081.7, 1095.7, 1111.7, and 1127.7 or a combination of such compounds is employed to suppress an immune response associated with an organ or tissue transplantation, autoimmune disease, or a non-autoimmune inflammatory disease. In a particular example, a biologically active agent including colutellin A (molecular mass of 1127.7) is utilized to suppress an immune response, such as one affiliated with an organ or tissue transplantation, autoimmune disease, or a non-autoimmune inflammatory disease.

In a further example, the biologically active agents can be used to control diverse fungal pathogens including, but not limited to, *Rhizoctonia solani, Botrytis cinerea*, and *Sclerotinia sclerotiorum*. For example, a biologically active agent including an endophytic *Colletotrichum* sp. compound such as colutellin A, colutellin B, colutellin C, colutellin D or a combination of such compounds is employed to control fungi including *Rhizoctonia solani, Botrytis cinerea*, and *Sclerotinia sclerotiorum*. In a particular example, a biologically active agent including colutellin A (molecular mass of 1127.7) is utilized to control fungi, such as *Rhizoctonia solani, Botrytis cinerea*, and *Sclerotinia sclerotiorum*. For example, the biologically active agents including an endophytic *Colletotrichum* sp. compound (such as an endophytic *Colletotrichum* sp. compound with a molecular mass of 1081.7, 1095.7, 1111.7, and 1127.7 or a combination of such compounds) can be used to treat or protect plants challenged or infected by any myriad of plant pathogens, such as pathogenic fungi, and may be used to treat diseases in the field, soil or in post harvest applications. Additional agricultural applications include, but are not limited to, treatment in seed coats, on agricultural implements, leaf or plant surfaces, and building or other material surfaces—generally, any site which may contain or come into contact with a pathogen.

VI. Methods of Production

The present disclosure also relates to methods for producing the described biological agents. The biological agents may be an endophytic *Colletotrichum* sp.; an extract of the endophytic *Colletotrichum* sp.; or a compound (e.g., a cyclic lipopeptide) obtained from the endophytic *Colletotrichum* sp., e.g., compound with a molecular mass of 1081.7, 1095.7, 1111.7, and 1127.7 or a combination of the compounds thereof, having the biological activity of interest. Representative methods include cultivating an isolate of an endophytic *Colletotrichum* sp. and recovering the cells or a biological agent from the culture medium. It may be desirable thereafter to form the free acid or a salt or ester by methods known by one of ordinary skill in the art.

The endophytic *Colletotrichum* sp., or a high yielding or otherwise modified mutant thereof, may be used in the methods of the present disclosure to produce biologically active agents.

In an example, the endophytic *Colletotrichum* sp. is cultivated in a nutrient medium suitable for production of the heterologous biological substance using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection).

In one example, the nutrient media for the cultivation of the endophytic *Colletotrichum* sp. contains, in the range of about 0.1 to about 10%, a complex organic nitrogen source such as yeast extract, corn steep liquor, vegetable protein, seed protein, hydrolysates of such proteins, milk protein hydrolysates, fish and meat extracts, and hydrolysates such as peptones. In an alternative example, chemically defined sources of nitrogen can be used such as urea, amides, single or mixtures of common amino acids such as valine, asparagine, glutamic acid, proline, and phenylalanine. In further examples, carbohydrates (0.1-5%) are included in the nutrient media and starch or starch hydrolysates such as dextrin, sucrose, lactose or other sugars or glycerol or glycerol esters may also be used. The source of carbon can be derived from vegetable oils or animal fats. Carboxylic acids and their salts can be included as a source of carbon for growth and production of β-lactamase inhibitors. A particularly suitable low cost medium is one containing soy bean flour plus dried malt distillers solubles plus dextrin.

In an example, mineral salts such NaCl, KCl, $MgCl_2$, $ZnCl_2$, $FeCl_3$, $Na_2SO_4$, $FeSO_4$, $MgSO_4$ and $Na^+$ or $I^+$ salts of phosphoric acid are added to the media described above particularly if chemically defined. In further examples, $CaCO_3$ (as a source of $Ca^{++}$ ions or for its buffering action), salts of trace elements (such as nickel, cobalt or manganese) or vitamins are added to the media.

The present disclosure is also directed to a mutant of an endophytic *Colletotrichum* sp. wherein the amount of the biological activity agent produced by the mutant is greater than the amount of the substance produced by a corresponding parental strain. The present disclosure is further directed to methods for obtaining such a mutant. In one example, an endophytic *Colletotrichum* sp. is obtained from a mutant of an endophytic *Colletotrichum* sp. strain, wherein the substance is produced in an amount greater than the amount of the substance produced by a corresponding parental strain. Suitable methods of producing mutant strains are well-known to those in the art, and include, for example, ionizing radiation (such as gamma-rays or X-rays), UV light, UV light plus a photosensitizing agent (such as 8-methoxypsoralen), nitrous acid, hydroxylamine, purine or pyrimidine base analogues (such as 5-bromouracil and N-methyl-N'-nitro-N-nitrosoguanidine), acridines, alkylating agents (such as mustard gas, ethyl-methane sulphonate), hydrogen peroxide, phenols, formaldehyde, and heat. Alternatively, mutants may be produced through genetic techniques such as recombination, shuffling, transformation, transduction, lysogenisation, lysogenic conversion, and selective techniques for spontaneous mutants. Specifically, one method of mutating an endophytic *Colletotrichum* sp. strain and selecting such a mutant comprises the following procedure: (i) the parental strain is treated with a mutagen; (ii) the thus presumptive mutants are grown in a medium suitable for selection of a mutant strain; and (iii) the mutant strain is selected on the basis of increased production of a compound of the present disclosure. In a specific example, the selected colonies are grown in a normal production medium, and a final selection for such mutants is performed.

The present disclosure also relates to methods for obtaining a "substantially pure" endophytic *Colletotrichum* sp. compound, such as an endophytic *Colletotrichum* sp. compound which contains less than 5% contaminants. For example, the substantially pure endophytic *Colletotrichum* sp. compound contains at least 95% of one of the disclosed compounds (a compound with a molecular mass of 1081.7, 1095.7, 1111.7, and 1127.7 or combination thereof). In an example, endophytic *Colletotrichum* sp. isolate, or other compounds of endophytic *Colletotrichum* sp., are extracted from the culture filtrate by a variety of methods known to the art. In a specific example, the cells of the endophytic *Colletotrichum* sp. are first removed from the fermentation by filtration or centrifugation before such extraction procedures are commenced. Precipitation by solvent extraction from culture filtrate, which may use an adjusted to acid pH values and methods based on the anionic nature of the metabolite such as the use of anion exchange resins can be utilized. Other primary methods of isolation which may be used include conventional methods such as adsorption onto carbon, precipitation, salting out, molecular filtration, or any method known in the art.

VII. Compositions

The present disclosure also relates to compositions comprising a biological agent as described herein. The biological agent may be an endophytic *Colletotrichum* sp., an extract of the endophytic *Colletotrichum* sp., or a compound, such as a cyclic lipopeptide, obtained from the endophytic *Colletotrichum* sp., e.g., a compound with a molecular mass of 1081.7, 1095.7, 1111.7, and 1127.7 (such as colutellin A, B, C, and D) or a combination thereof, having the biological activity of interest. The composition can include a suitable carrier, or may comprise the agent affixed to a substrate. The compositions including a biologically active agent of the present disclosure can be used to control a range of pathogenic organisms (such as fungi), diseases, or conditions. The composition can also find use as applied to a substrate. The agent is provided in an amount effective to inhibit the pathogenic organism or condition for a time and under conditions permitting the agent to inhibit the pathogenic organism or condition. Different compositions will be required for administration to plants, humans and animals in unit dosage forms, such containing suitable quantities of the compounds.

Common carriers and excipients include, but are not limited to, corn starch or gelatin, lactose, sucrose, microcrystalline cellulose, kaolin, mannitol, dicalcium phosphate, sodium chloride, and alginic acid.

The endophytic *Colletotrichum* sp. isolate or other compounds, or a salt or ester thereof, obtainable from an endophytic *Colletotrichum* sp. can be formulated into a pharmaceutical composition, which comprises the compound, together with a pharmaceutically acceptable carrier.

The compound may be in the form produced by the endophytic *Colletotrichum* sp., or the result of further chemical modification, for instance to reduce toxicity and perhaps to increase efficacy or availability (e.g., availability in a biological system, such as a subject). This approach has been effectively taken with antibiotic family, obtained from a plant associated microbe—*Pseudomonas syringae*, namely, the pseudomycins (Ballio et al., *FEBS Letters* 355, 96-100, 1994). A specific pseudomycin has been subjected to modifications by organic synthesis and has yielded a derivative that is no longer toxic to mammalian systems and yet remains effective against human pathogenic fungi (Zhang et al., *Bioorg. Med. Chem. Lett.* 11, 123-126, 2001; Zhang et al., *Bioorg. Med. Chem. Lett.* 11, 903-907, 2001).

VIII. Administration of Compositions

The pharmaceutical compositions of the disclosure include those in a form adapted for oral, topical, or other potential use, and may be used for immunosuppression in animals, particularly mammals including but not limited to humans.

Examples of suitable unit dosage forms in accord with the present disclosure are tablets, capsules, pills, suppositories, powder packets, wafers, granules, cachets, teaspoonfuls, tablespoonfuls, dropperfuls, ampoules, suspensions, syrups, vials, aerosols with metered discharges, segregated multiples of any of the foregoing, and other forms as herein described. Such compositions may contain conventional pharmaceutically acceptable materials such as diluents, binders, colors, flavors, preservatives, disintegrants and the like in accordance with conventional pharmaceutical practice in the manner well understood by those skilled in the art of formulating pharmaceutical compounds. The concentration of a compound in the unit dosage may vary, for example, from about 1 percent to about 50 percent depending on the particular form of the compound and its solubility and the dose desired.

For oral administration, either solid or fluid unit dosage forms can be prepared. For preparing solid compositions such as tablets, the desired compound is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Disintegrators commonly used in the compositions of the disclosure include croscarmellose, microcrystalline cellulose, corn starch, sodium starch glycolate, and alginic acid. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum, or other inert oil.

Fluid unit dosage forms for oral administration such as syrups, elixirs, and suspensions can also be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose, and the like.

Tablet binders that can be included are acacia, methylcellulose, sodium carboxymethylcellulose, poly-vinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils, and colloidal silica.

Flavoring agents such as peppermint, oil of wintergreen, cherry flavoring, or the like can also be used. It may be desirable to add a coloring agent to make the dosage form more attractive in appearance or to help identify the product.

For parenteral administration, fluid unit dosage forms are prepared utilizing the compound and a sterile vehicle, with water being preferred. The compound, depending on the vehicle and concentration used, can be either suspended or dissolved in the vehicle. In preparing solutions, the compound can be dissolved in water for injection and filtered sterilized before filling into a suitable vial or ampoule and sealing. Advantageously, adjuvants such as a local anesthetic, preservative, and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the compound. This dosage form is of particular interest where the mammal cannot be treated conveniently by means of other dosage forms, such as orally or by insufflation, as may be the case of animals, or young children, or debilitated persons. The compound can be incorporated into any of the known suppository bases using methods known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 gm.

Typically, any effective quantity of a compound of the present disclosure is employed in treatment. The determination of an appropriate dosage of the compound for a given treatment depends on many factors that are well known to those skilled in the art. They include for example, the route of administration and the potency of the particular compound.

The particular compound may be present in the composition as the sole therapeutic agent or may be present together with other therapeutic agents, either related or unrelated to the original compound.

A convenient method of practicing the treatment method may be to administer a compound of the present disclosure via intravenous (IV) infusion. In this procedure, a sterile formulation of a suitable soluble salt of the compound is incorporated in a physiological fluid, such as 5% dextrose solution, and the resulting solution is infused slowly by IV administration. Alternatively, the piggy-back method of IV infusion can also be used. For IV use, a water soluble form of the antibiotic can be dissolved in one of the commonly used intravenous fluids and administered by infusion. Such fluids as, for example, physiological saline, Ringer's solution, or 5% dextrose solution can be used.

For intramuscular preparations, a sterile formulation of a suitable soluble salt form of the compound, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, for example, an ester of a long chain fatty acid such as ethyl oleate.

A composition comprising a compound of the present disclosure (e.g., an endophytic *Colletotrichum* sp. isolate, such as a cyclic lipopeptide) can be administered in a single daily dose or in multiple doses per day. The treatment regimen may require administration over extended periods of time, for example, for several days or weeks (such as for one to six weeks). The amount per administered dose or the total amount administered will depend on such factors as the nature and severity of the infection, the age and general health of the patient, the tolerance of the patient to the compound.

IX. Exemplary Uses of Compositions

Compositions as described herein may be used for immunosuppression or to treat a fungal infection in an organism, such as a plant.

Suppression of an Immune Response

Provided, then, are compositions and methods for suppressing an immune response in an organism (e.g., mammal), which comprises administering to the organism a therapeutically effective amount of an endophytic *Colletotrichum* sp. isolate, such isolate C-12, a compound (such as a cyclic lipopeptide (e.g., colutellin A)), or a salt or ester thereof. For example, the composition including endophytic colutellin A is useful for suppressing an immune response associated with an organ or tissue transplantation, autoimmune disease, or a non-autoimmune inflammatory disease. For example, the composition including endophytic colutellin A, B, C, D or a combination thereof suppresses the immune response by at least 10%, such as at least 20%, at least 30%, at least 50%, or at least 70%.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like. Further, exemplary inflammatory diseases affecting mammals include rheumatoid arthritis, osteoarthritis, inflammatory lung disease (including chronic obstructive pulmonary lung disease), inflammatory bowl disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like. In particular examples, a therapeutically effective amount of an endophytic *Colletotrichum* sp. isolate, such isolate C-12, a compound (such as a cyclic lipopeptide (e.g., colutellin A)), or a salt or ester thereof is administered to suppress suppressing an immune response associated with at least or combination thereof of the aforementioned diseases. The method includes administering to the subject an amount of a compound of the present disclosure which is effective for this purpose. In general, an effective amount is a dose between about 0.5 and about 100 mg/kg. A particular dose is from about 1 to about 60 mg/kg of active compound. A typical daily dose for an adult human is from about 1 mg to about 50 mg.

Treatment of Fungal Infections

Also provided are compositions and methods of treating fungal infection in an organism, such as a plant or mammal, which comprises administering to the organism an anti-fungal effective amount of an endophytic *Colletotrichum* sp. compound, such as a cyclic lipopeptide (e.g., colutellin A), or a salt or ester thereof. The compositions can also be used to control diverse fungal pathogens including, but not limited to, *Rhizoctonia solani, Botrytis cinerea*, and *Sclerotinia sclerotiorum*.

The compositions of the disclosure may be pesticidal compositions used for administration to plants, or the associated soil, equipment, containers, machinery, surfaces and so forth. For use with a plant, the method of use may involve applying an endophytic *Colletotrichum* sp. strain, or an extract or compound (e.g., peptide) derived from the strain either directly to the plant, or to soil adjacent to the plant. In some cases the treatment may be made to seeds, e.g., in the format of seed coats, soaks, or other such applications. In certain circumstances, the strain (rather than an extract) can be applied to grow in association with the plant and produce biologically active compounds capable of protecting the plant against plant pathogen attack, such as fungal attack.

The present disclosure is further directed to pesticidal compositions comprising the substance in an effective amount to control a pest, and a pesticidal carrier. For example, an effective amount is the amount of the substance sufficient to control a pest through killing or stunting of the growth of the pest or protecting a plant from pest infestation. The pesticidal compositions may comprise a compound of the present disclosure in a substantially pure form or as an extract from a whole broth culture of an endophytic *Colletotrichum* sp. in dry, concentrated, or liquid form and a suitable pesticidal carrier, examples of which are disclosed infra. The substance is present in the composition at a concentration of about 0.001% to about 60% (w/w).

The pesticidal compositions may further comprise a deposition agent which assists in preventing the composition from drifting from the target area during application (e.g., as it is sprayed from a plane), or from being blown away from the plant once it has been deposited. The deposition agent in the compositions of the present disclosure is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions of the present disclosure in an amount of between about 0.4% w/w and about 50% w/w, preferably between about 1% w/w and about 20% w/w.

The pesticidal compositions may further comprise an antifreeze/humectant agent which suppresses the freeze point of the product and helps minimize evaporation when sprayed and which maintains deposit texture making the product more efficacious and palatable. Examples of antifreeze/humectant agents include, but are not limited to, ethylene glycol, propylene glycol, dipropylene glycol, glycerol, butylene glycols, pentylene glycols and hexylene glycols. When utilized, the antifreeze/humectant agent is present in the pesticidal compositions of the present disclosure in an amount of between about 0.5% w/w and about 25% w/w, preferably between about 2% w/w and about 15% w/w.

The pesticidal compositions may further comprise a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are non-ionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols. Further examples of such surfactants are cationic surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions may further comprise an inert material. Examples of inert materials include inorganic minerals such as diatomaceous earth, kaolin, mica, gypsum, fertilizer, phyllosilicates, carbonates, sulfates, or phosphates; organic materials such as sugars, starches, or cyclodextrins; or botanical materials such as wood products, cork, powdered corncobs, rice hulls, peanut hulls, and walnut shells.

The pesticidal compositions may further comprise a preservative, a feeding stimulant, an attractant, an encapsulating pesticide, a binder, a dye, an ultraviolet light protectant, a buffer, a flow agent, or other component to facilitate product handling and application for particular target pests.

The pesticidal compositions can be applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending upon the nature of the particular composition, specifically, whether it is a concentrate or to be used directly. The composition may contain about 1% to about 98% of a solid or liquid inert carrier. The compositions will be preferably administered at the labeled rate for commercial products, preferably about 0.01 pound to 5.0 pounds per acre when in dry form and at about 0.01 pint to 25 pints per acre when in liquid form.

The pesticidal compositions can be applied directly to a plant by, for example, spraying or dusting at the time when the pest has begun to appear on the plant or before the appearance of pests as a protective measure. The pesticidal compositions can be applied by foliar, furrow, broadcast granule, "lay-by", or soil drench application. The compositions can also be applied directly to ponds, lakes, streams, rivers, still water, and other areas subject to infestation by pests of concern to public health. The compositions can be applied by spraying, dusting, sprinkling, or the like. The spray or dust can conveniently contain another pesticide.

The pesticidal compositions can be applied to protect a number of different plant types, including, but not limited to, cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fiber plants (cotton, flax, hemp, jute), citrus fruit (oranges, lemons, grapefruit, mandarins), other fruits (such as bananas, pineapples, cassayas, mangos, guavas, grapes, and so forth), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, and natural rubber plants, as well as ornamental plants as well as ornamental plants and particularly plants which are grown for their flowers. It will be appreciated that the listed plants are representative only, rather than limiting.

The present disclosure is further described by the following examples, which should not be construed as limiting the scope of the disclosure.

Example 1

Materials and Methods

This example provides a description of the material and methods utilized for the isolation and characterization of *Colletotrichum* sp.

Isolating, culturing, identifying, and storing of *Colletotrichum* sp. The culture of *Colletotrichum* sp. was obtained as an endophyte from a small cutting made on an immature *Pteromischum* sp. plant collected in a Caribbean costal Costa Rican rainforest. A number of other plant samples, including *Dipteryx* sp., *Monstera* sp. and *Cercopia* sp and others were collected at the same time and in the same area. Each plant sample was given a numerical designation. Endophytes were recovered from each plant made in the collection using the standard methods of surface treatment, tissue removal and plating on water agar (Strobel & Daisy, *Microbiol. Mol. Biol. Rev.* 67: 491-502, 2003). One fungus, designated CR-12, was recovered from *Pteromischum* sp. and when grown on potato dextrose agar (PDA) was initially shown to have antimycotic activity by virtue of a bioassay test (Castillo et al., *Microbial Ecol.* 53: 12-19, 2007). The organism was examined for its morphological and spore-forming features as described below for taxonomic purposes. In addition, molecular biological studies were performed on this fungus. It was grown on PD broth for 7 days and the mycelium was harvested and the DNA was extracted using the DNeasy Plant and Fungi Mini kit (QIAGEN®) according to the manufacturer's directions. The ITS regions of the fungus were amplified using PCR and the universal ITS primers ITS1 (59-TCC GTA GGT GAA CCT GCG G-39; SEQ ID NO: 2) and ITS4 (59-TCC TCC GCT TAT TGA TAT GC-39; SEQ ID NO: 3). All other procedures were carried out as described by Ezra et al. (*Microbiology* 150: 4023-4031, 2004). Sequence data were deposited in GenBank (GenBank Accession No. EU330193).

Plugs containing the mycelium were placed in 15% glycerol and stored at −70° C. However, the other storage conditions for the fungus were obtained by growing the fungus on sterilized barley and placing the infested grains at −70° C. The fungus was deposited as No. 2341 in the living mycological culture collection at Montana State University.

Test fungi and bacteria. All plant pathogenic fungi used in the bioassay test system were obtained from Drs. Don Mathre and Nina Zidak of the MSU Department of Plant Sciences. All fungi were grown on potato dextrose agar (PDA) at 23° C. and only freshly transferred cultures (4-7 days old) were used in the fungal bioassay tests.

Scanning electron microscopy (SEM). Isolate CR-12 was grown on PDA and later processed for SEM. Many agar pieces containing the fungus were placed into filter paper packets and suspended in 2% glutaraldehyde in 0.1 M sodium cacodylate buffer (pH 7.2-7.4) with Triton X (a wetting agent). Tissues were aspirated for 5 min. and incubated overnight as previously described (Ezra et al., *Microbiol.* 150: 4023-4031, 2004). Ultimately, for SEM some of the fungal material was critical point dried, gold sputter coated and images were recorded with an FEI XL30 ESEM FEG in high vacuum mode using the Everhart-Thornley detector. Freshly prepared wet specimens were examined by environmental scanning electron microscopy (ESEM) and images were recorded with an FEI XL30 ESEM FEG in the environmental mode as described by Castillo et al. (*Scanning* 27: 305-311, 2005). A gaseous electron detector was used with a spot size of 3, at 15 kV. The temperature was 40° C. with a chamber pressure which ranged from 5 to 6 Torr providing humidity up to 100% at the sample. Conidia were measured using Image J software (available online at web address rsb.info.nih.gov/ij/).

Minimum inhibitory concentrations (MICs). Assays were performed in sterile 24-well plates with each well containing 500 µl of potato dextrose broth. The plates were incubated from 48-288 hours at 25 C. The MIC was defined as the minimum concentration of compound resulting in no visible growth of the test organism. The compounds were dissolved in methanol which represented less than 0.5% total methanol in each test well. Several small plugs of agar 3×3×3 mm containing actively growing test fungi were then placed into each well with some wells serving as controls.

Bioassay guided isolation and purification of colutellin. *Colletotrichum* sp. (171) was grown in shake culture for 28 days at 25° C. The fungal mycelium was removed from the fermentation broth by filtration and extracted three times with equal volumes of n-butanol. The bioactivity of the extract/fraction was evaluated by placing a small amount of material on a PDA plate and challenging with several plugs of agar supporting the growth of *Botrytis cinerea* (bioassay guided fractionation). Approximately 40 g (dry wt) of the extract was fractionated by liquid chromatography on a 5.0×28.0 cm column of silica gel (Selecto Scientific—particle size 32-63) using 700 ml of each solvent system in a stepwise gradient of increasing polarity (A) methylene chloride 100%; (B) chloroform 100%; (C) chloroform: ethyl acetate 50:50 v/v; (D) ethyl acetate 100%; (E) ethyl acetate: ethanol 50:50 v/v; (F) ethanol 100% and (G) methanol 100%. Three fractions (B, C, D) were the most active in the antifungal assay (100 µg/ml). These active fractions were flash evaporated to dryness and were again chromatographed on a 3.0×58.0 cm silica column (same material and same solvent program) eluted with 11 of each of the solvent systems A, B, C, D to obtain 8 active subfractions (ca. 400 ml each) using an identical elution profile as before. The sub-fraction at 1.3-1.6 l was obtained by virtue of its bioactivity against *B. cinerea*. It was further purified by semipreparative HPLC on a Waters 600E HPLC with a Phenomenex Sphereclone column 5 µODS (250×10 mm) under gradient conditions (flow: 5 ml min$^{-1}$, 0 min H$_2$O:methanol 50:50 v/v; 20 min methanol 100%; 40 min acetonitrile 100%). Detection was at 220 nm and the most biologically active product eluted in a distinct single peak at 24.6 min and it yielded only one compound with a mass of 1127.7 (colutellin A). This compound was used for all biological assays and chemical analysis. However, other biological activity remained before and after this peak (broad peak) at 1.1-1.9 l as sub-fractions of the second silica column and it too was subjected to HPLC and the main peak had a retention time of 23.9 min, it possessed colutellin A and 3 other colutellin A-like derivatives. This peak was subjected to LC/MS analysis.

General instrumental procedures. Ultraviolet (UV) spectra were recorded in 100% methanol using a Beckman DU-50 UV-visible spectrophotometer. Spectra by NMR were recorded on a Varian INOVA AS-600 MHz spectrometer, using the signals of the residual solvent protons as internal references ($\delta_H$ 3.3 and $\delta_H$ 4.9 ppm for deuterated MeOH) at 23° C. Masses were determined on an LTQ FT ULTRA (Thermo Scientific). Samples were suspended in 50% (v/v) acetonitrile, 0.1% (v/v) formic acid at a concentration of 10 pmol/μl, and introduced into the instrument by nanoelectrospray at a flow rate of 50 nl/min. Tandem mass spectrometry and desalting studies were done on a QSTAR system from Applied Biosystem (QqTOF). For desalting, measurements were taken before and after sample application to a ZipTip® C18 (Millipore Corp.). MALDI-TOF studies were performed on a Vayager DESTR MALDI-TOF instrument (Applied Biosystems). Samples and matrix (α-cyano-4-hydroxycinnamic acid) were mixed at a ratio of 1:1 (v/v) before being spotted onto the MALDI plate and air dried. Electrospray mass spectral data also were acquired using a Micromass LCT TOF mass spectrometer.

Amino acid analysis and Edman sequencing methods. Samples for amino acid analysis were dissolved in 50% (v/v) methanol-water and subjected to hydrolysis and analysis, essentially as described (Castillo et al., *FEMS Lett.* 255: 296-300, 2006). Automated Edman sequencing was performed on an Applied Biosystems cLC system.

Immunosuppression and toxicity tests. Colutellin A, in matched studies with cyclosporin A, was examined for its ability to inhibit the activation of CD4±T cells for the production of IL-2 (Umland et al., *Am. J. Respir. Cell Mol. Biol.* 20: 481-492, 1999; Clark et al., *J. Immunol.* 162: 2546-2554, 1999). This test is commonly taken as an indication of the potential that a compound may act as an immunosuppressant (Umland et al., *Am. J. Respir. Cell Mol. Biol.* 20: 481-492, 1999; Clark et al., *J. Immunol.* 162: 2546-2554, 1999). Total spleen cells were isolated from C57/B 6 mice and then were preactivated with ConA (1 ug/mL, Sigma-Aldrich, St. Louis, Mo.) for 2 days. These cells were then treated for 4 hours with cross-linked Hamster anti-mouse CD3/CD28 (1 ug/mL, BD Bioscience) antibodies in the Bruff's Medium containing 5% fetal bovine serum and 1× brefeldin A. After the activation, cells were fixed and analyzed for IL-2 production in the activated CD4± T cells using APC-conjugated anti-mouse IL-2 and PE-conjugated anti-mouse CD4 antibodies by flow cytometry. In like manner, in matched studies, both colutellin A and cyclosporin A were examined for their toxicity profiles. Blood was collected from healthy adult donors and peripheral blood mononuclear cells (PBMCs) were purified using Histopaque 1077 (Sigma Aldrich, St. Louis, Mo.) according to the manufacturer's instructions. The cells, PBMCs, were cultured at 1×10⁶ cells/ml in X-vivo 15 medium (Cambrex, Walkersville, Md.) with varying concentrations of cyclosporin A, colutellin A or equivalent amounts of DMSO for 24 or 48 hours. Cells were washed twice with PBS followed by staining with Annexin V directly conjugated to PE or FITC and 7-AAD using the Annexin V Apoptosis Detection Kit I (BD Biosciences, San Jose, Calif.) as per the manufacturer's instructions. Cells were then subjected to flow cytometry on a FACS Calibur equipped with an HTS loader (BD Biosciences, San Jose, Calif.). The staining allowed for differentiation among viable, necrotic and apoptotic cells. The studies were repeated at least three times and the variation between the dead cells detected was recorded as a function of concentration over 24 and 48 hour test periods.

Example 2

Isolation of Fungal Endophytes

This example describes the isolation of fungal endophytes.

Each of the plants collected in the Costa Rican rainforest yielded a large collection of endophytic fungi. The stem tissues of *Pteromischum* sp., however, supported the growth of a number of fungal colonies that proved to be identical to each other and are collectively labeled CR-12. No other plant in the same area yielded this fungus. The colonies were brownish, round and discrete. Multiple sporodochia were located throughout the surface of the fungal colonies. Each sporodochium had several large setae possessing echinulated surfaces. The conidiophores were located close together and were macronematous to mononematous and irregularly branched. The conidia were aggregated in slimy masses. Each conidium was cylindrical and slightly curved and rounded or slightly tapered at the ends. For critical point dried specimens the spores averaged 19.1×2.1 μm. Images obtained by ESEM were approximately the same length, but averaged 2.68 μm in diameter (FIG. 1). Thus, it is apparent that the methods used to prepare specimens for regular SEM caused some shrinkage of the spores. On the basis of these initial morphological characteristics this dematiaceous hyphomycetous fungus was identified as *Volutella* sp. (Pers.) Sacc. having synonymy with other named genera including *Sarcopodium, Psilonia, Tricholeconium, Thelephora* and *Conoplea* (Ellis, More Dematiaceous Hyphomycetes Commonwealth Mycological Institute, KEW, England, pg 507, 1976).

Upon further review and molecular characterization studies this dematiaceous hyphomycetous fungus was identified as *Colletotrichum* sp. instead of as *Volutella* sp. Further identification of CR-12 was done using an ITS-5.8S rDNA analysis followed by a BLAST search. These studies indicated that the closest relatives (at the 98% level) of this fungus are various isolates of *Colletotrichum* spp., including *Colletotrichum graminicola*, and *Colletotrichum capsici* (*C. capsici*). Since *C. graminicola* is a fungal species designated for isolates of *Colletotrichum* that are pathogenic on corn (*Zea mays*), CR-12 was not given this species designation. However, CR-12 is also genetically related to *C. capsici*. It turns out that *C. capsici* is also a pathogenic fungus. Some researchers prefer to place non-pathogenic *C. capsici*-like fungi as a form of *C. dematium*, which is usually considered as a non-pathogenic taxon with slightly narrower conidia than *C. capsici* (Sutton, *The Coelomycetes*. Kew, UK: CMI 1980). The conidial shape and size of CR-12 were also consistent with the assessment that this isolate be designated *C. dematium*.

The rDNA sequences of CR-12 were deposited in GenBank under GenBank accession number EU330193 (as available on Jul. 17, 2008) which is hereby incorporated by reference in its entirety as of Nov. 6, 2008. Because of its ability to inhibit a number of pathogenic fungi, using a simple assay test, this endophytic *Colletotrichum* sp. was selected for further study of its extracellular bioactive components by methods well known to those of skill in the art and as described in the Examples 3 and 4 below.

Example 3

Isolation and Characterization of *Colletotrichum* sp. Endophytes

This example describes the isolation and characterization of an endophytic *Colletotrichum* sp.

Figure 2:
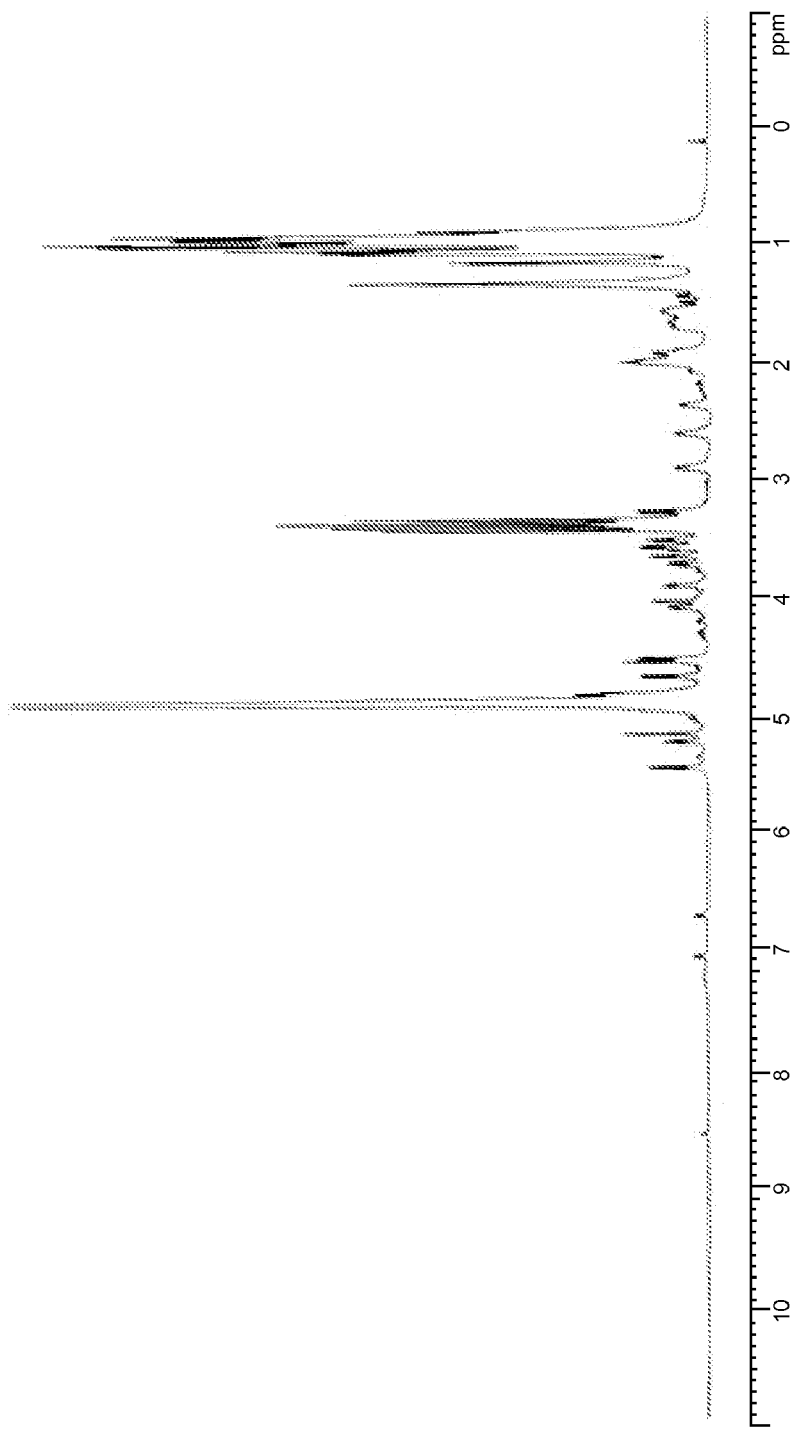
Figure 3:
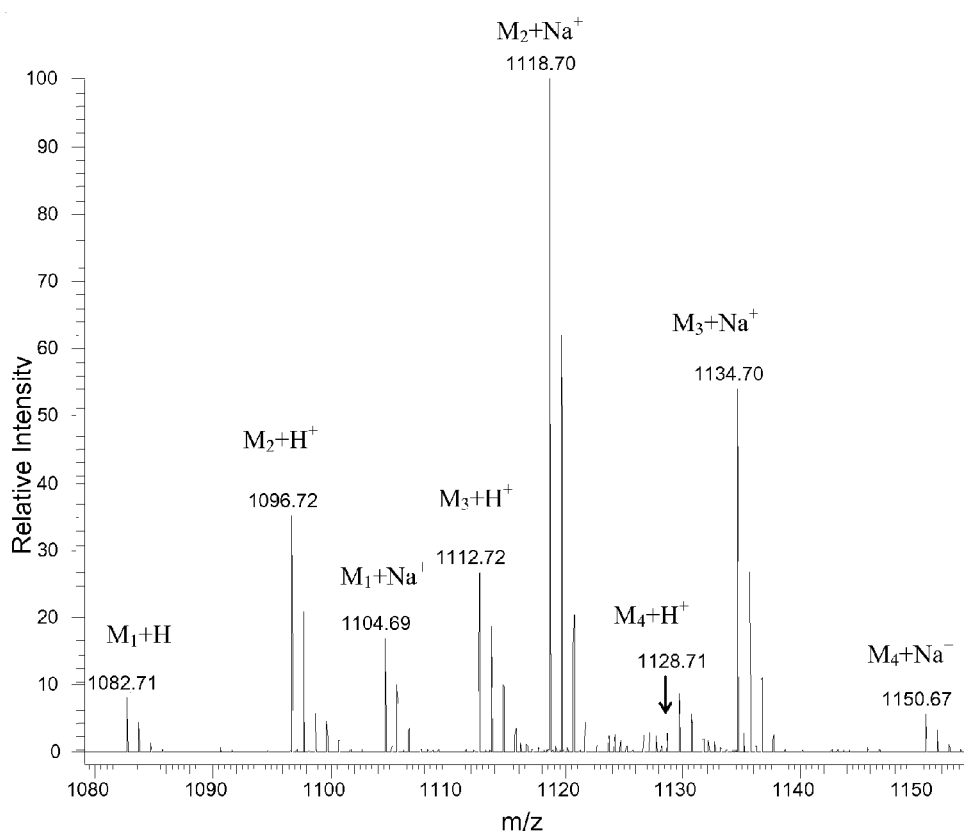

The isolate C-12 of an endophytic *Colletotrichum* sp. yielded about 0.45 mg/l of colutellin A (eluting from the HPLC column at 24.6 minutes) which possessed antimycotic activity. The compound had a mass of 1127.70 and a sole millimolar UV extinction at 210 nm with ε=1,014. This absorptivity is associated with the peptide bond and since no absorption bands appeared at 280 nm the compound was presumed not to possess any aromatic amino acids (Silverstein et al., *Spectrometric Identification of Organic Compounds* Wiley & Sons, N.Y. pg 419, 1991). The NMR-proton spectrum was characteristic of a peptide having aliphatic carbons along with more down field resonances occurring with carbon atoms bearing protons with adjoining nitrogen and oxygen atoms (FIG. 2) (Silverstein et al., *Spectrometric Identification of Organic Compounds* Wiley & Sons, N.Y. pg 419, 1991). The compounds found in the broad silica-gel/HPLC peak at 23.9 min were subjected to ESI-QqTOF and LTQ-FT mass spectrometry revealing both singly- and doubly-charged molecular ions of mass 1081.7, 1095.7, 1111.7, and 1127.7, of which the 1095.7 peak was the most prominent (FIG. 3). Sodium adducts of these molecules, all of which were 22 atomic mass units (amu) higher in mass (FIG. 3), also were observed, the intensities of which were substantially reduced by desalting. Mass differences of 14 and 16 amu among the ions suggest that the compounds are related by the presence or absence of oxygen or methylene groups, the latter of which would be a common variation among lipopeptides with the lipid component being modified. These compounds were not further examined. Quantitative amino acid analysis of colutellin A revealed the presence of Ile, Val, Ser, N-methyl-Val, and β-amino-isobutryic acid in nominal molar rations of 3:2:1:1:1, respectively. Both Edman and mass spectrometric sequencing that revealed an N-terminal tetrapeptide sequence Val-Ile-Ser-Ile (SEQ ID NO: 1) and a tripeptide sequence Ile-Pro-Val. Signal levels of the first four amino acids were significant during Edman sequencing, thus the lack of additional sequence suggested the peptide was blocked, likely by native cyclization. The cyclic nature of the peptides was supported by the added observations that colutellin A reacted poorly with ninhydrin (faint pink spot upon heating) and that sodiated ions were observed by Micromass LCT TOF mass spectrometry which is common for cyclic peptides.

An examination of the Chapman Hall database revealed that there are a number of known compounds with masses of 1127 including aureofungin A, halichrondrin C, norhalichrondrin A, deisobutrylolivomycin A, onchidin, partricin A, mepartricin B tetrocarin F and vacidin A. None of these compounds matches the complete description of the peptide made by *Colletotrichum* sp. described herein. Furthermore, there were no direct matches in the database for the other observed masses of 1081.7, 1095.7, or 1111.7. Therefore, this novel compound was named—colutellin A after its source fungal organism. Also, in contrast, cyclosporin A has a mass of 1202.6 which is 75 mass units lower than colutellin. Furthermore, colutellin A is not a derivative of cyclosporin A in that it does not possess such residues, among others such as alanine, and N-methyl leucine. Thus, it appears that colutellin A represents a family of related lipopeptides and one of which has a mass of 1127.7.

Example 4

Biological Activities of Colutellin A

This example describes the biological activities of colutellin A.

Because colutellin A had certain characteristics resembling those of cyclosporin A (cyclic peptide with antifungal activity) all biological assays were conducted in matched studies. Both of the compounds possess strong inhibitory activity against *Botrytis cinerea* and *Sclerotinia sclerotiorum* which remains stable up to 288 hours (Table 1). The result with *S. sclerotiorum* is in close agreement with that of Rodríguez et al. (*J. Appl. Microbiol.* 100: 575-86, 2006) who reported that cyclosporin A possessed an MIC of 0.1 µg per disc. Harel et al. (*Mol. Plant. Microbe. Interact.* 6: 682-693, 2006) showed that calcineurin plays a major role in both sclerotial development and pathogenesis of *S. sclerotiorum*. The calcineurin pathway maybe involved in the pathogenic potential of this major fungal pathogen (Steinbach et al., *Nat. Rev. Microbiol.* 6: 418-430, 2007). It has been suggested that cyclosporin A may affect *S. sclerotiorum* by virtue of inhibiting the calcineurin pathway. This may also be true of colutellin A since they have comparable patterns of antimycotic activity (Table 1). These findings support the possible use of *Botrytis* and *Sclerotinia* as a quick initial system for screening organisms for the production of immunosuppressants.

Both cyclosporin A and colutellin A possess a relatively narrow spectrum of antimycotic activity with some organisms such as *Pythium ultimum* and *Trichoderma viride* not being affected and others are quite sensitive (Table 1). Overall, it is also worth noting that although the test fungi are nicely matched relative to their sensitivities to the two compounds examined, the MIC values of cyclosporin A and colutellin A are, in some cases, more than 50 times different (Table 1). This suggests that the compounds may have different molecular targets within some of the test organisms.

TABLE 1

Minimum Inhibitory Concentrations (MICs) of Colutellin A and Cyclosporin A on Common Fungal Pathogens

| Fungus tested | Cyclosporin A MIC (µg/ml) (After h) | | | Colutellin A MIC (µg/ml) (After h) | | |
|---|---|---|---|---|---|---|
| | 48 h | 144 h | 288 h | 48 h | 144 h | 288 h |
| *Pythium ultimum* | >100 | >100 | >100 | >100 | >100 | >100 |
| *Trichoderma virde* | >100 | >100 | >100 | >100 | >100 | >100 |
| *Sclerotinia sclerotiorum* | 0.07 | 0.1 | 0.1 | 3.6 | 10.8 | 32.4 |
| *Botrytis cinerea* | 0.07 | 0.1 | 0.1 | 3.6 | 10.8 | 10.8 |
| *Fusarium solani* | >100 | >100 | >100 | 7.2 | >100 | >100 |
| *Rhizoctonia solani* | 1.2 | 10.8 | 10.8 | >100 | >100 | >100 |
| *Aspergillus fumigatus* | 1.2 | 3.6 | 3.6 | 2.4 | >100 | >100 |
| *Geotrichum canididum* | >100 | >100 | >100 | 3.6 | >100 | >100 |

Both colutellin A and cyclosporin A were examined for their ability to inhibit the IL-2 production by activated CD4±T cells. Generally, the inhibition of IL-2 production is directly related to the ability of a compound to act in a whole biological system as an immunosuppressant (Umland et al., *Am. J. Respir. Cell Mol. Biol.* 20: 481-492, 1999; and Clark et al., *J. Immunol.* 162: 2546-2554, 1999).

Using all of the appropriate controls and various concentrations of colutellin A and cyclosporin A, IL-2 production for each compound was plotted and then calculated in mouse spleen cells activated with ConA. The $IC_{50}$ for cyclosporin A was 61.8 nM and for colutellin A it was 167.3 nM. The $IC_{50}$ of colutellin A is in the same range as cyclosporin A giving an indication that colutellin A possesses immunosuppressive properties.

Figure 4:
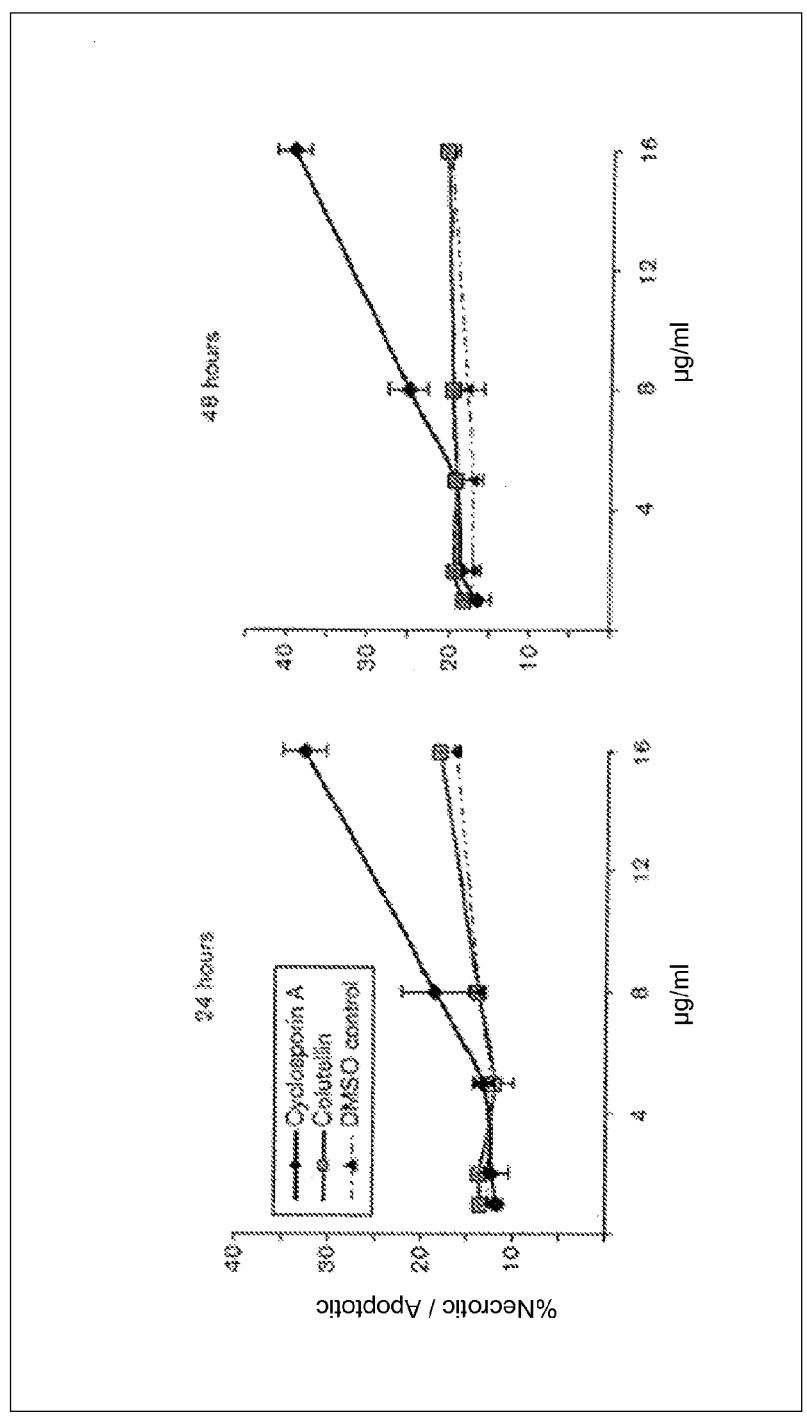

As a result of the enormous importance of cyclosporin A as the first widely used immunosuppressive compound, a search for other natural products with similar activity was initiated. Although a large number of natural products have demonstrated immunosuppressant activity, most studies have not included the corresponding cytotoxic activity of the reported compounds (Mann, *Nat. Product Repts.* 18: 417-430, 2001). Interestingly, the use of cyclosporin A in clinical settings has to be carefully monitored because of its cytotoxic activity. In this regard, its toxicity was compared with colutellin A in studies with human peripheral blood mononuclear cells (PBMCs). Cyclosporin A exhibited a higher level of cytotoxicity on human PBMCs than colutellin A or DMSO alone after 24 and 48 hours of culture (FIG. 4). Specifically, in repeated tests, at concentrations at or above Bug/ml cyclosporin induces significant levels of both necrosis and apoptosis, whereas colutellin A did not induce significant cell death above the DMSO controls at any concentration tested (FIG. 4).

Because of the immense importance of cyclosporin A to medicine, a comprehensive search was undertaken to find other organisms producing cyclosporin A and/or its derivatives. At least 28 natural cyclosporins have been discovered being produced by 25 different fungal taxa (Lawen et al., *Biochem. J.* 300: 395-399, 1994; Jegorov et al., *Phytochem.* 38: 403-407, 1995; Traber et al., *J. Ind. Microbiol. &Biotech.* 17: 397-401, 1996). Some of these include: *Acremonium lunulae, Aphanocladium* sp., *Beauveria brongniarti, Chaunopycnis alba, Cylindrotrichum oligospermum, Cylindrocarpon lucidum, Fusarium oxysporum, Fusarium solani, Isaria felina, Neocosmospora africana, Paecilomyce* spp., *Stachybotrys chartarum*, and *Tolypocladium* spp. (Sakamoto et al., *J. Antibiot.* 46: 1788-1798, 1993; Dreyfuss and Chapela., *Biotech.* 26: 49-80.1994; Jegorov et al., *Phytochem.* 38: 403-407, 1995; Traber et al., *J. Ind. Microbiol. &Biotech.* 17: 397-401, 1996). In addition, about 800 semisynthetic or synthetic analogs have been produced and tested in vitro, but only a few of them were worth testing in vivo (Rehacek, *Folia Microbiol* 40: 68-88 1995). Most of the immunosuppressant compounds isolated from nature are lipopeptides, cyclic peptides, or cyclic lipopeptides, but few have low cytotoxicity accompanied with high immunosuppressive activity. This fact makes colutellin A a desirable drug, since it has little or no toxicity and significant immunosuppressive activity.

Example 5

Method of Suppressing an Immune Response

This example illustrates a representative method of suppressing or inhibiting an immune response, such as an immune response associated with an organ or tissue transplantation, an autoimmune disease or a non-autoimmune inflammatory disease.

According to the teachings herein, one can prevent, suppress, or inhibit an immune response by administering an endophytic *Colletotrichum* sp. isolate from a *Pteromischum* sp. plant, or a composition including one or more *Colletotrichum* sp. compounds (such as a cyclic lipopeptide). For example, a subject who is in need of immunosuppression, such as a subject with an autoimmune disease, a non-autoimmune inflammatory disease or an organ or tissue transplant recipient is selected. A therapeutically effective amount of a *Colletotrichum* sp. isolate (such as C-12 isolate) or compound (such as a compound including a *Colletotrichum* sp. isolate with a molecular mass of 1081.7, 1095.7, 1111.7, 1127.7 or a combination of two or more such compounds) is administered to the subject to prevent, inhibit, or suppress the immune response associated with the disease or the transplantation. An effective amount of the *Colletotrichum* sp. isolate or compound to be used will depend, at least, on the particular method of use, the subject being treated, the severity of the infection, and the manner of administration of the therapeutic composition. For example, this can be the amount of the *Colletotrichum* sp. isolate or compound necessary to prevent, inhibit, or suppress an immune response associated with the given condition. Ideally, a therapeutically effective amount is an amount sufficient to prevent, inhibit, or suppress the immune response without causing a substantial cytotoxic effect on host cells. The compounds are prepared as described herein. In a specific example, the *Colletotrichum* sp. isolate or compound (such as a *Colletotrichum* sp. compound including colutellin A) is administered to prevent, inhibit, or suppress an immune response associated with an autoimmune disease, non-autoimmune disease or an organ or tissue transplantation. For example, the composition including endophytic colutellin A, B, C, D or a combination thereof suppresses the immune response by at least 10%, such as at least 20%, at least 30%, at least 50%, at least 70%, at least 80%, at least 90% or at least 95%.

Exemplary autoimmune diseases affecting mammals include rheumatoid arthritis, juvenile oligoarthritis, collagen-induced arthritis, adjuvant-induced arthritis, Sjogren's syndrome, multiple sclerosis, experimental autoimmune encephalomyelitis, inflammatory bowel disease (e.g., Crohn's disease, ulcerative colitis), autoimmune gastric atrophy, pemphigus vulgaris, psoriasis, vitiligo, type 1 diabetes, non-obese diabetes, myasthenia gravis, Grave's disease, Hashimoto's thyroiditis, sclerosing cholangitis, sclerosing sialadenitis, systemic lupus erythematosis, autoimmune thrombocytopenia purpura, Goodpasture's syndrome, Addison's disease, systemic sclerosis, polymyositis, dermatomyositis, autoimmune hemolytic anemia, pernicious anemia, and the like. Further, exemplary inflammatory diseases affecting mammals include rheumatoid arthritis, osteoarthritis, inflammatory lung disease (including chronic obstructive pulmonary lung disease), inflammatory bowl disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like. In particular examples, a therapeutically effective amount of an endophytic *Colletotrichum* sp. isolate, such isolate C-12, a compound (such as a cyclic lipopeptide (e.g., colutellin A)), or a salt or ester thereof is administered to suppress suppressing an immune response associated with at least one or combination thereof of the aforementioned diseases.

Example 6

Methods of Protecting a Plant from a Plant Pathogen

This example illustrates methods of protecting a plant from a plant pathogen including use of pesticidal compositions and compounds.

Based upon the teachings herein, one can protect a plant from a plant pathogen by use of at least one isolated strain of *Colletotrichum* sp. which is an endophyte of a *Pteromischum* sp. plant or compounds and compositions including one of the disclosed endophytic *Colletotrichum* sp. compounds. For example, pesticidal compounds and compositions including *Colletotrichum* sp. compounds with a molecular mass of 1081.7, 1095.7, 1111.7 and 1127.7 or a combination of two or more such compounds are administered to plants, or the associated soil, equipment, containers, machinery, surfaces and the like to protect plants from plant pathogens. Plant pathogens can include, but are not limited to, *Botrytis cinerea, Sclerotinia sclerotiorum*, and *Rhizoctonia solani*. For use with a plant, the method involves applying an isolated *Colletotrichum* sp. strain or an extract or compound derived from the isolate either directly to the plant, or to soil adjacent to the plant. In some cases the treatment is made to seeds, e.g., in the format of seed coats, soaks, or other such applications. In certain circumstances, the isolate (rather than an extract or compound) is applied to grow in association with the plant and produce the biologically active compounds capable of protecting the plant against plant pathogen attack.

An effective amount of the isolate, extract, compound or composition can be the amount required to control a pest. For example, an effective amount is the amount of the substance sufficient to control a pest through killing or stunting of the growth of the pest or protecting a plant from pest infestation. The pesticidal compositions can include an endophytic *Colletotrichum* sp. compound (such as a peptide) in a substantially pure form or as an extract from a whole broth culture of an endophytic *Colletotrichum* sp. strain in dry, concentrated, or liquid form and a suitable pesticidal carrier. The substance is present in the composition at a concentration of from about 0.001% to about 60% (w/w).

The pesticidal compositions can also include a deposition agent which assists in preventing the composition from drifting from the target area during application (e.g., as it is sprayed from a plane), or from being blown away from the plant once it has been deposited. The deposition agent in the compositions is preferably a proteinaceous material, which has the added benefit of being palatable to the insect. Any animal or vegetable protein is suitable for this purpose, in dry or in liquid form. Examples of useful sources of protein which can be conveniently and economically added to the composition include, but are not limited to, soy protein, potato protein, soy flour, potato flour, fish meal, bone meal, yeast extract, and blood meal. Alternative deposition agents include modified cellulose (carboxymethylcellulose), botanicals (grain flours, ground plant parts), non-phyllosilites (talc, vermiculite, diatomaceous earth), natural clays (attapulgite, bentonite, kaolinite, montmorillonite), and synthetic clays (Laponite). When utilized, the deposition agent is present in the pesticidal compositions disclosed above in an amount of between about 0.4% w/w and about 50% w/w, preferably between about 1% w/w and about 20% w/w.

The pesticidal compositions can also include an antifreeze/humectant agent which suppresses the freeze point of the product and helps minimize evaporation when sprayed and which maintains deposit texture making the product more efficacious and palatable. Examples of antifreeze/humectant agents include, but are not limited to, ethylene glycol, propylene glycol, dipropylene glycol, glycerol, butylene glycols, pentylene glycols and hexylene glycols. When utilized, the antifreeze/humectant agent is present in the pesticidal compositions of the present disclosure in an amount of between about 0.5% w/w and about 25% w/w, preferably between about 2% w/w and about 15% w/w.

In addition, a pesticidal composition can include a surfactant in an amount where it acts as an emulsifying, a wetting, or a dispersing agent. Examples of such surfactants are anionic surfactants such as carboxylates, for example, a metal carboxylate of a long chain fatty acid; N-acylsarcosinates; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g., butyl naphthalene sulphonate; salts or sulphonated naphthalene-formaldehyde condensates; salts of sulphonated phenol-formaldehyde condensates; or more complex sulphonates such as amide sulphonates, e.g., the sulphonated condensation product of oleic acid and N-methyl taurine or the dialkyl sulphosuccinates, e.g., the sodium sulphonate or dioctyl succinate. Further examples of such surfactants are non-ionic surfactants such as condensation products of fatty acid esters, fatty alcohols, fatty acid amides or fatty-alkyl- or alkenyl-substituted phenols with ethylene oxide, block copolymers of ethylene oxide and propylene oxide, acetylenic glycols such as 2,4,7,9-tetraethyl-5-decyn-4,7-diol, or ethoxylated acetylenic glycols. Further examples of such surfactants are cationic surfactants such as aliphatic mono-, di-, or polyamine as acetates, naphthenates or oleates; oxygen-containing amines such as an amine oxide of polyoxyethylene alkylamine; amide-linked amines prepared by the condensation of a carboxylic acid with a di- or polyamine; or quaternary ammonium salts. When utilized, the surfactant is present in an amount of between about 0.5% w/w and about 25% w/w, preferably between about 1% w/w and about 8% w/w.

The pesticidal compositions can also include an inert material, preservative, a feeding stimulant, an attractant, an encapsulating pesticide, a binder, a dye, an ultraviolet light protectant, a buffer, a flow agent, or other component to facilitate product handling and application for particular target pests as described above.

The pesticidal compositions are applied in a dry or liquid form, e.g., a suspension, a solution, an emulsion, a dusting powder, a dispersible granule, a wettable powder, an emulsifiable concentrate, an aerosol or impregnated granule, or a concentrate or primary composition which requires dilution with a suitable quantity of water or other diluent before application. The concentrations of each component in the composition will vary depending upon the nature of the particular composition, specifically, whether it is a concentrate or to be used directly. The composition can contain about 1% to about 98% of a solid or liquid inert carrier. In an example, the compositions are administered at the labeled rate for commercial products, preferably about 0.01 pound to 5.0 pounds per acre when in dry form and at about 0.01 pint to 25 pints per acre when in liquid form.

In one example, the pesticidal compositions are applied directly to a plant by, for example, spraying or dusting at the time when the pest has begun to appear on the plant or before the appearance of pests as a protective measure. Alternatively, the pesticidal compositions are applied by foliar, furrow, broadcast granule, “lay-by”, or soil drench applications. Additional applications include applying the compositions directly to ponds, lakes, streams, rivers, still water, and other areas subject to infestation by pests of concern to public health by spraying, dusting, sprinkling, or the like. The spray or dust can conveniently contain another pesticide.

The pesticidal compositions are applied to protect a number of different plant types, including, but not limited to, cereals (wheat, barley, rye, oats, rice, sorghum and related crops), beets (sugar beet and fodder beet), drupes, pomes and fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fiber plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes), lauraceae (avocados, cinnamon, camphor), deciduous trees and conifers (linden-trees, yew-trees, oak-trees, alders, poplars, birch-trees, firs, larches, pines), or plants such as maize, turf plants, tobacco, nuts, coffee, sugar cane, tea, vines, hops, bananas and natural rubber plants, as well as ornamental plants and particularly plants which are grown for their flowers.

Deposit of Biological Material

If necessary, strains disclosed herein will be deposited under conditions that assure that access to the culture(s) will be available during the pendency of this patent application to one determined by the Commissioner of Patents and Trademarks to be entitled thereto under 37 C.F.R. §1,14 and 35 U.S.C. §122. Each deposit will represent a substantially pure culture of the deposited strain. However, it should be understood that the availability of a deposit does not constitute a license to practice the subject disclosure in derogation of patent rights granted by governmental action. All restriction on the availability to the public of the material so deposited will be irrevocably removed upon the granting of a patent.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the disclosure are to be understood to be applicable to any other aspect, embodiment, or example of the disclosure. Accordingly, this disclosure includes all modifications encompassed within the spirit and scope of the disclosure as defined by the following claims.

The invention claimed is:

1. An isolated peptide obtained from *Colletotrichum dematium*, wherein the peptide has a molecular mass of about 1127.7 Da and a tetrapeptide sequence Val-Ile-Ser-Ile (SEQ ID NO:1).

2. The peptide of claim 1, wherein the *Colletotrichum dematium* is isolated from a *Pteromischum* sp. plant, and has antifungal or immunosuppressive activity.

3. The peptide of claim 1, wherein the peptide has biological activity against a fungal plant pathogen.

4. The peptide of claim 3, wherein the fungal plant pathogen is at least one of *Botrytis cinerea, Sclerotinia sclerotiorum*, or *Rhizoctonia solani*.

5. A crude extract which comprises the peptide according to claim 1.

6. The crude extract of claim 5, wherein the extract has biological activity against a fungal plant pathogen.

7. The crude extract of claim 6, wherein the fungal plant pathogen is selected from the group consisting of *Botrytis cinerea, Rhizoctonia solani*, and *Sclerotinia sclerotiorum*.

8. The peptide of claim 1, wherein the peptide contains residues of Ile, Val, Ser, N-methyl-Val and beta-aminoisobutryic acid in nominal molar ratios of 3:2:1:1:1, respectively.

9. An isolated peptide obtained from *Colletotrichum dematium*, wherein the peptide has a molecular mass of about 1127.7 Da and contains residues of Ile, Val, Ser, N-methyl-Val and beta-aminoisobutryic acid in nominal molar ratios of 3:2:1:1:1, respectively, and a tetrapeptide sequence Val-Ile-Ser-Ile (SEQ ID NO:1).

* * * * *